United States Patent [19]

Garrow

[11] Patent Number: 4,665,566
[45] Date of Patent: May 19, 1987

[54] ADJUSTABLE STRAP WITH FASTENERS FOR ATTACHMENT OF MEDICAL TUBING

[76] Inventor: Geraldine E. Garrow, Rte. 1, Dry Creek Rd., Boise, Id. 83703

[21] Appl. No.: 820,653

[22] Filed: Jan. 21, 1986

[51] Int. Cl.⁴ .............................................. A42B 1/00
[52] U.S. Cl. ..................................... 2/171; 2/DIG. 6; 2/DIG. 11; 128/201.22
[58] Field of Search .................. 2/2.1 R, 68, DIG. 6, 2/DIG. 11, 171; 128/200.24, 201.22

[56] References Cited

U.S. PATENT DOCUMENTS

| | | | |
|---|---|---|---|
| 1,056,988 | 3/1913 | Greene | 128/201.11 |
| 4,273,130 | 6/1981 | Simpson | 2/DIG. 6 |
| 4,393,519 | 7/1983 | Nicastro | 2/DIG. 6 |
| 4,447,912 | 5/1984 | Morrow | 2/DIG. 6 |
| 4,495,663 | 1/1985 | Shieh | 128/201.11 X |

Primary Examiner—Louis K. Rimrodt

[57] ABSTRACT

A device comprised of a strip of material to be placed about the head or an extremety of a patient and adjustably fastened thereto. The band has positioned about its circumference a plurality of fasteners by which medical tubing is securely and conveniently fastened to the patient.

2 Claims, 5 Drawing Figures

ADJUSTABLE STRAP WITH FASTENERS FOR ATTACHMENT OF MEDICAL TUBING

BACKGROUND OF THE INVENTION

1. Field of the Invention

The invention generally pertains to an improved method of attaching Nasal Oxygen Cannulas and other medical tubings to a patient's head and/or extremeties.

2. Brief Description of Prior Art

Nasal oxygen cannulas are generally attached to a patient's head by means of a narrow elastic band which is a part of the cannula. Many times the elastic band is too tight around the patient's head and the band loses its elasticity with use. These bands are uncomfortable, do not hold the cannula in place adequately, and do not hold additional tubing that may be used about the head. Nasal gastric tubes and nasal feeding tubes in the past have been taped to a patient's forehead or cheek with resultant irritation of the skin. Intravenous tubing has classically been taped to a patient's arm or leg. The tape causes skin irritation and does not hold the tubing comfortably or adequately. This invention eliminates these problems in all the above mentioned uses.

SUMMARY OF THE INVENTION

This invention relates to a device which facilitates attachment of nasal oxygen cannulas, nasogastric tubes, nasalgastric feeding tubes, Intravenous tubing and the like to a patient's head or extremeties. The strap consists of a strap which is adjusted to the size of the head or extremeties by means of a velcro fastener. Velcro fasteners attached to the strap are closed around the tubing of the nasal oxygen cannula or the like. An adhesive backed Velcro fastener may be attached to the tubing and the strip then closed within the Velcro fasteners to prevent slippage.

It is the object of the invention to provide a more convenient, comfortable and secure method of attaching medical tubing used in and about the face or extremeties of a patient.

BRIEF DESCRIPTION OF THE DRAWINGS

FIG. 3 is a view showing the strap as worn by a patient using a nasogastric tube, nasal feeding tube or the like;

DESCRIPTION OF THE PREFERRED EMBODIMENT

Figure 1:
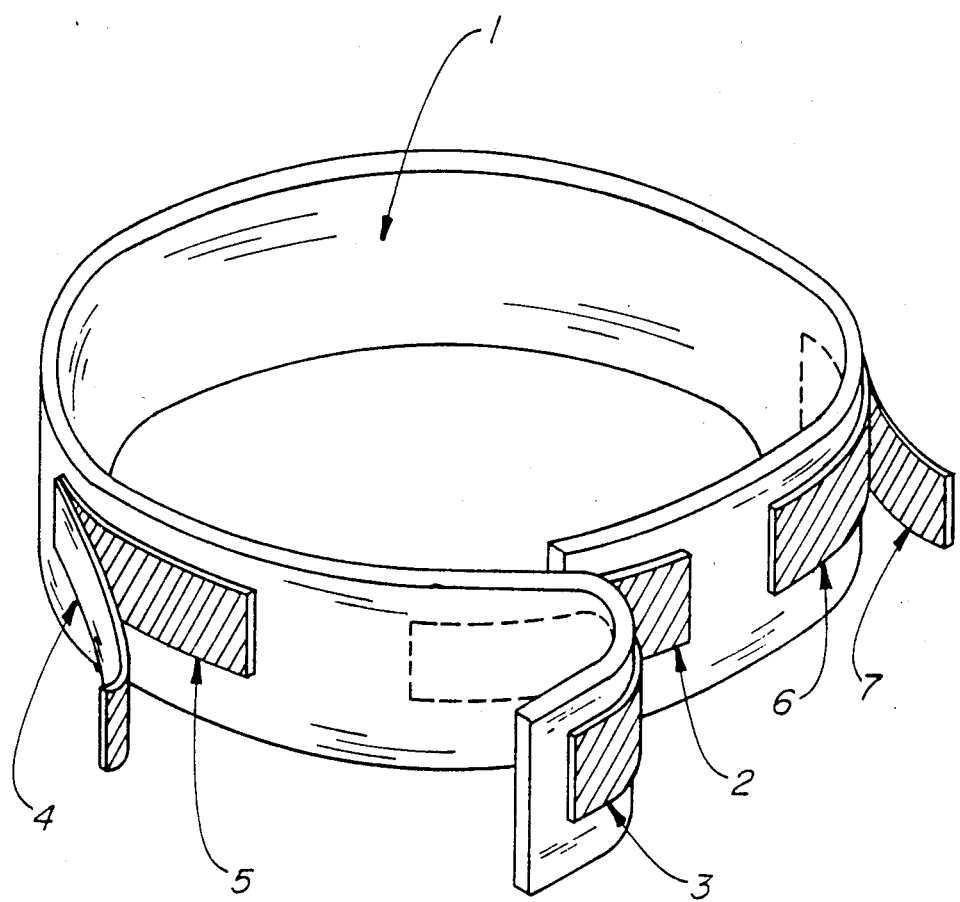
FIG. 1 is a view showing the strap with adjustable velcro fastener open and velcro strips for attachment of medical tubing in the open position.
Figure 2:
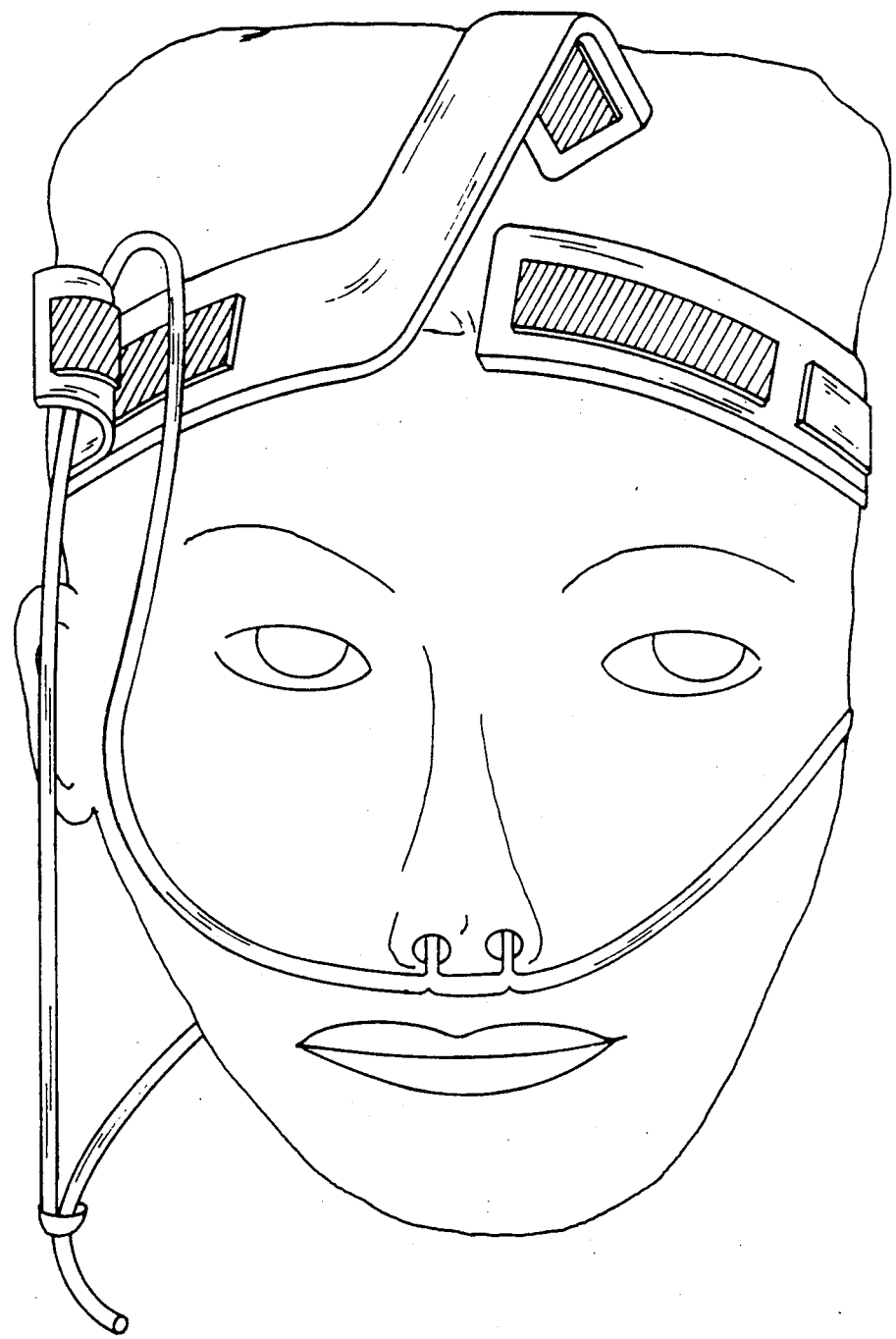
FIG. 2 is a view showing the strap as worn by a patient using a nasal oxygen cannula.
Figure 3:
Figure 4:
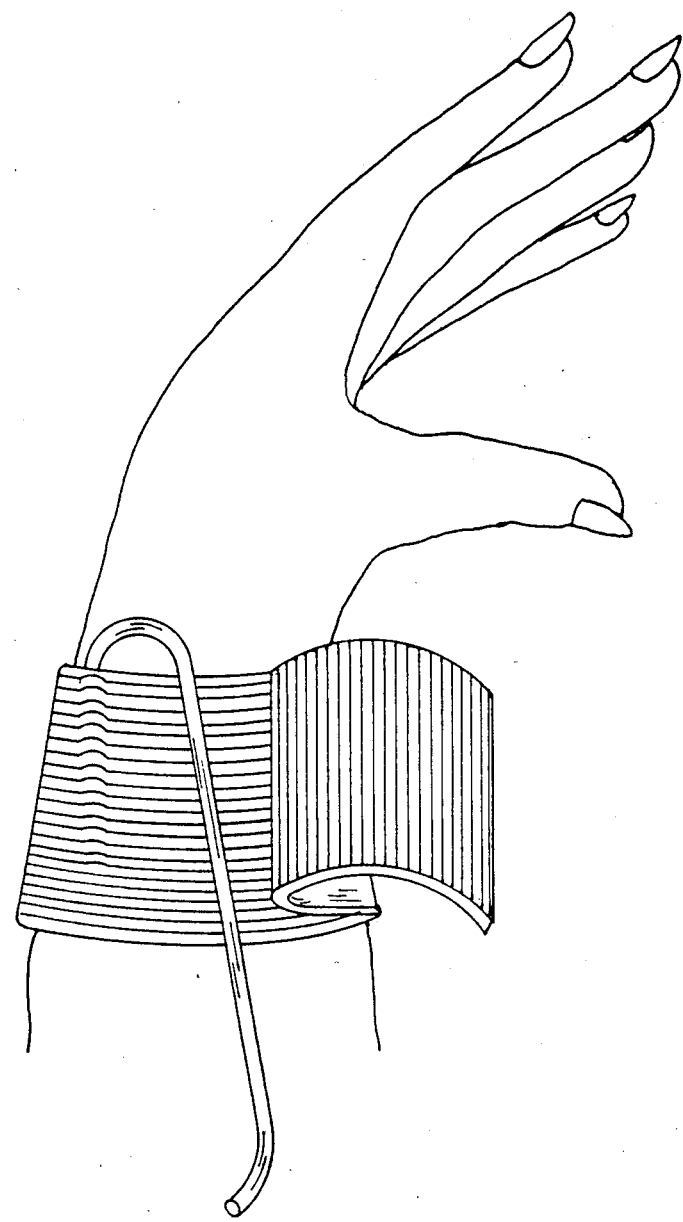
FIG. 4 is a view showing the strap as worn by a patient upon an extremety using the strap to hold an intravenous tubing.
Figure 5:
FIG. 5 is a view showing a hat in which the Velcro fasteners for attachment of medical tubing are located about its circumference.

Referring to FIGS. 1, 2, 3, 4, 5 and 6, and embodiment of the Adjustable Strap for the attachment of medical tubings.

In this embodiment, a strap 1 is shown which contacts the patient's head or another extremety when it is on the patient. For purposes of this invention the term patient includes any person and persons of all ages. The strap 1 is attached to the patient by means of adjustable Velcro fasteners, 2 and 3. These fasteners 2 and 3 can be any suitable fastener used to attach two ends of a strap. In this embodiment the Velcro fasteners 4 and 7 are pressed over the medical tubing and secure it to the strap by attachment to the Velcro fasteners 5 and 6. These fasteners 4 and 5 and 6 and 7 may be made of tie strings, snap fasteners or any other suitable fastening means. The Velcro fastener 2 and 3 is positioned for adjustment over the patient's forehead or the anterior portion of any other extremety for ease of attachment. In other embodiments the Velcro fasteners 2 and 3 may be located at any position around the circumference of the strap. The velcro fasteners 4 and 5 and 6 and 7 are located laterally from velcro fastener 2 and 3 on the side of strap 1 which does not touch the patient's skin. This invention contemplates any number and position of Velcro fasteners like 4 and 5 and 6 and 7 upon the Strap 1. The strap 1 may be manufactured from any suitable material. All the Velcro fasteners are sewn to the Strap 1 by means of a thread of any suitable material, however any suitable means of binding or attaching the fasteners to the Strap 1 are contemplated in this embodiment. Other embodiments contemplate the replacement of strap 1 with an elastic band or a hat wherein Velcro fasteners 4 and 5 and 6 and 7 are attached about the circumference of the band or hat as described for strap 1.

In some cases it is desireable to prevent the tubing which is attached to the strap 1 by means of fasteners 4 and 5 and 6 and 7 from slipping. It is contemplated then that in some embodiments a Velcro fastener with adhesive backing will be attached to a tube by means of the adhesive backing and this Velcro fastener 8 would then be closed within Velcro fasteners 4 and 5 and 6 and 7.

Although one detailed embodiment of the invention is illustrated in the drawings and previously described in detail, this invention contemplates any configuration, design and relationship of components which will function in a similar manner and which will provide the equivalent result.

I claim:

1. A device for attaching medical tubing to a patient's forehead or other extremety which comprises:
 a. a strap device comprised of a generally flat strip of material having two ends and a side which does not touch the patients skin;
 b. means of adjustably fastening the two ends of the strip of material together so that when fastened the strip of material forms an opening to encompass the head or extremety of the patient;
 c. medical tubing fastener means attached to the side of the strap which does not touch the patient's skin whereby medical tubing may be securely and conveniently fastened to the patient.

2. A strap device as recited in claim 1 in which the means of fastening is comprised of Velcro fasteners.

* * * * *